(12) United States Patent
Wakata et al.

(10) Patent No.: US 8,108,080 B2
(45) Date of Patent: Jan. 31, 2012

(54) MONITORING AND CONTROL APPARATUS AND METHOD AND WIND POWER PLANT EQUIPPED WITH THE SAME

(75) Inventors: Daisuke Wakata, Tokyo (JP); Akira Yasugi, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 12/903,291

(22) Filed: Oct. 13, 2010

(65) Prior Publication Data

US 2011/0140428 A1    Jun. 16, 2011

Related U.S. Application Data

(63) Continuation of application No. PCT/JP2010/059091, filed on May 28, 2010.

(51) Int. Cl.
*G05D 3/12*  (2006.01)
*G05D 5/00*  (2006.01)
*G05D 9/00*  (2006.01)
*G05D 11/00* (2006.01)
*G05D 17/00* (2006.01)
*F03D 9/00*  (2006.01)
*H02P 9/04*  (2006.01)

(52) U.S. Cl. ............. 700/286; 700/287; 290/44; 290/55
(58) Field of Classification Search .......... 700/286–287; 290/44, 55; 416/37, 43
See application file for complete search history.

(56) References Cited

U.S. PATENT DOCUMENTS

| 5,083,039 | A  | * | 1/1992  | Richardson et al. ............ 290/44 |
| 6,724,097 | B1 |   | 4/2004  | Wobben |
| 6,924,565 | B2 | * | 8/2005  | Wilkins et al. ................. 290/44 |
| 6,925,385 | B2 | * | 8/2005  | Ghosh et al. ..................... 702/14 |
| 7,372,173 | B2 | * | 5/2008  | Lutze et al. ..................... 290/44 |
| 7,649,282 | B2 |   | 1/2010  | Jurkat et al. |
| 7,677,869 | B2 | * | 3/2010  | Martinez De Lizarduy Romo et al. .............................. 416/37 |
| 7,915,762 | B2 | * | 3/2011  | Helle et al. ....................... 307/87 |
| 8,033,788 | B2 | * | 10/2011 | Egedal et al. ................... 416/43 |
| 2007/0124025 | A1 | * | 5/2007  | Schram et al. ................ 700/287 |
| 2008/0048501 | A1 | * | 2/2008  | Jurkat et al. .................... 307/81 |
| 2008/0174180 | A1 | * | 7/2008  | Jurkat et al. .................... 307/80 |
| 2009/0096211 | A1 | * | 4/2009  | Stiesdal ......................... 290/44 |

(Continued)

FOREIGN PATENT DOCUMENTS

JP    2003-079057    3/2003

(Continued)

OTHER PUBLICATIONS

ISR for PCT/JP2010/059091 dated Jun. 29, 2010.

*Primary Examiner* — Ronald Hartman, Jr.
(74) *Attorney, Agent, or Firm* — Kanesaka Berner & Partners

(57) ABSTRACT

It is an object to reduce influence on a utility grid by reducing a rapid change in active power, and to extend the life of a wind power plant while controlling active power output in response to a request from the utility grid. A monitoring and control apparatus applied to a wind power plant including a plurality of wind turbine generators includes an electric power control unit that controls the wind turbine generators so as to reduce output of the wind power plant in a stepwise manner, when an active power reduction request from a utility grid side is output.

14 Claims, 4 Drawing Sheets

U.S. PATENT DOCUMENTS

| | | | |
|---|---|---|---|
| 2009/0102195 A1* | 4/2009 | Altemark et al. | 290/44 |
| 2009/0180875 A1* | 7/2009 | Egedal et al. | 416/43 |
| 2009/0234510 A1* | 9/2009 | Helle et al. | 700/287 |
| 2010/0274401 A1* | 10/2010 | Kjaer et al. | 700/287 |
| 2010/0308585 A1* | 12/2010 | Jorgensen et al. | 290/44 |

FOREIGN PATENT DOCUMENTS

| | | |
|---|---|---|
| JP | 2009-156171 | 7/2009 |
| JP | 2009-303355 | 12/2009 |

* cited by examiner

| (THRESHOLD VALUE) | LOAD-FATIGUE EVALUATION INDEX | INSULATION-FATIGUE EVALUATION INDEX |
|---|---|---|
| GROUPA | $a < \alpha$ | $d < \beta$ |
| GROUPB | $b < \alpha \leq a$ | $e < \beta \leq d$ |
| GROUPC | $\alpha \leq b$ | $\beta \leq e$ |
| GROUPD | — | — |

MONITORING AND CONTROL APPARATUS AND METHOD AND WIND POWER PLANT EQUIPPED WITH THE SAME

This application claims the benefit of International Patent Application No. PCT/JP2010/059091, the content of which is incorporated herein by reference.

TECHNICAL FIELD

The present invention relates to a monitoring and control apparatus and method and a wind power plant equipped with the same.

BACKGROUND ART

In general, a wind power plant having a plurality of wind turbine generators have a monitoring and control apparatus for controlling the power generation level of the whole wind power plant to respond to an output limit requested from the utility grid side. For example, Patent Literature 1 proposes a method for responding to an output request from the utility grid by accommodating, among the wind power plants, the generated power obtained from individual wind power plants by using a monitoring and control apparatus that centrally controls the plurality of wind power plants.

CITATION LIST

Patent Literature

{PTL 1} Japanese Unexamined Patent Application, Publication No. 2009-156171

SUMMARY OF INVENTION

Technical Problem

However, the method of Patent Literature 1 described above copes with generated power that cannot be accommodated among the wind power plants by controlling all wind turbine generators included in a predetermined wind power plant. In this case, when the active power of all the wind turbine generators in the wind power plant is reduced at once, this method has the problem in which a rapid change in active power is caused and greatly influences the utility grid. In addition, the method of Patent Literature 1 limits the output without distinguishing between wind turbine generators with a high level of degradation due to fatigue and so on and wind turbine generators having a low level of degradation. Since such wind turbine generators with a high level of degradation are not controlled for output limitation with priority, this method has the problem of being unable to extend the life of the wind power plant.

The present invention is made to solve the above problem, and it is an object thereof to provide a monitoring and control apparatus and method capable of reducing the influence on a utility grid by reducing the rapid change in active power, and extending the life of a wind power plant while controlling the active power output in response to a request of the utility grid, as well as a wind power plant equipped with the same.

Solution to Problem

To achieve the above object, the present invention provides the following solutions:

A first aspect of the present invention is a monitoring and control apparatus applied to a wind power plant including a plurality of wind turbine generators, comprising an electric power control unit that controls the wind turbine generators so as to reduce output of the wind power plant in a stepwise manner, when an active power reduction request from a utility grid side is output.

According to the first aspect, when the active power reduction request from the utility grid side is output, the output of the wind power plant is reduced in a stepwise manner. In this way, the rapid change in the active power caused when the active power of all the wind power generators in the wind power plant is reduced can be reduced, and thus the influence on the utility grid can be reduced.

The monitoring and control apparatus according to the first aspect may be configured to include a grouping section that groups the wind turbine generators in the wind power plant to form a plurality of groups. The electric power control unit may reduce the output of the wind power plant in a stepwise manner by instructing an output limit to the wind turbine generators per group in order.

With the above configuration, since the electric power control unit instructs the output limit to the wind turbine generators per group in order, the output of the wind power plant is reduced in a stepwise manner. In this way, the rapid change in the active power caused when the active power of all the wind power generators in the wind farm is reduced can be reduced, and thus the influence on the utility grid can be reduced.

The grouping section of the above configuration may be configured to group each of the wind turbine generators on the basis of a degradation level of each of the wind turbine generators.

With the above configuration, since the active power of the wind turbine generators in the group with a high level of degradation is reduced in order, reduction of the active power of the wind turbine generators in the group with a low level of degradation is delayed, which results in an increase in the life of the wind power plant.

The degradation level of the above configuration may be calculated on the basis of at least one of the load fatigue and the insulation fatigue of each of the wind turbine generators.

A second aspect of the present invention is a monitoring and control apparatus applied to a wind power plant including a plurality of wind turbine generators, comprising an estimating section that estimates degradation levels of each of the wind turbine generators; a grouping section that groups the wind turbine generators on the basis of the degradation levels to form the wind turbine generator groups; and an electric power control unit that reduces, upon receiving an active power reduction request from a utility grid side, the active power of the wind turbine generators included in a high degradation wind turbine generator group, which is the wind turbine generator group including the wind turbine generators with a high level of degradation, prior to the wind turbine generators included in the other wind turbine generator groups other than the high degradation wind turbine generator group.

According to this aspect, when an active power reduction request is received from the utility grid side, wind turbine generators in the high degradation wind turbine generator group, among the wind turbine generator groups grouped according to the degradation levels of the wind turbine generators, are reduced in active power prior to wind turbine generators in the other wind turbine generator groups. Here, the degradation levels refer to the degree of fatigue of the wind turbine generators determined depending on, for example, the frequency of failures of the wind turbine generators in the past, the frequency of warnings detected from the wind turbine generators in the past, and the poor response of the wind turbine generators.

Because the active power of a wind turbine generator group with a high level of degradation is reduced with priority in this way, for example, in the case where a wind power plant includes a plurality of wind turbine generators, which are grouped into a high degradation wind turbine generator group, an intermediate degradation wind turbine generator group, a low degradation wind turbine generator group, and the like, the active power of wind turbine generators included in the high degradation wind turbine generator group is reduced with priority. This can reduce a rapid change in active power caused when the active power of all the wind turbine generators in the wind power plant is reduced, thus reducing the influence on the utility grid. Furthermore, since the active power of a wind turbine generator group with a high level of degradation (that is, wind turbine generators with a high level of degradation due to operation) is reduced with priority, reduction of the active power of wind turbine generator groups with a low level of degradation (that is, wind turbine generators with a low level of degradation due to operation) is delayed, which results in an increase in the life of the wind power plant. Furthermore, reducing the active power in units of wind turbine generator groups decreases variations in active power per wind turbine generator, as compared with a case in which single wind turbine generators respond to active power reduction requests, thus reducing the influence on the utility grid.

The estimating section according to the above aspect may estimate the degradation levels on the basis of the power generation levels of the wind turbine generators; and the electric power control unit may treat the wind turbine generator group including the wind turbine generators with high power generation levels than the other wind turbine generators as the high degradation wind turbine generator group.

According to the above aspect, wind turbine generators with high power generation levels than the other wind turbine generators are treated as a wind turbine generator group with a high level of degradation. In the case where the wind turbine generator has a structure in which, for example, a main shaft joined to a rotor head fitted with wind turbine blades and rotating integrally therewith, a gearbox that increases the rotational speed of the main shaft and outputs the rotational torque, and a generator driven by the output of the gearbox are joined together to constitute a drivetrain, the relationship between the output of the wind turbine generator and the rotational torque of the main shaft is as shown in FIG. 4.

FIG. 4 shows a relationship in which a rotational torque exerted on the main shaft of the drivetrain increases as the output of the wind turbine generator increases. Since the degradation level (fatigue) of a wind turbine generator can be assessed from the level of the rotational torque exerted on the main shaft, a wind turbine generator group with a high level of degradation can easily be determined by estimating the degradation level on the basis of the output of the wind turbine generator, thereby extending the life of the wind power plant.

In the above aspect, in the case where the wind turbine generators each include a load reducing unit that reduces a load imposed on the wind turbine generators, the estimating section may estimate the degradation levels on the basis of the numbers of failures of the load reducing units; and the electric power control unit may treat the wind turbine generator group including the wind turbine generators that fail more than the other wind turbine generators as the high degradation wind turbine generator group.

According to the above aspect, since the active power of an inefficient wind turbine generator whose load cannot be reduced because of the influence of the failure of the load reducing unit is reduced, the life of the wind power plant can be extended. Here, examples of the load reducing unit include an individual pitch control unit, which is a unit for controlling the pitch angles of the wind turbine blades so as to reduce the load imposed on the wind turbine blades, and a tower damping control unit, which is a unit for controlling the damping of the wind turbine tower due to pitch angle control on the wind turbine blades.

In the estimating section according to the above aspect, the estimating section may estimate the degradation levels on the basis of the difference between a temperature detected from an insulator of the wind turbine generators and the temperature of the insulator detected during rated operation; and the electric power control unit may treat the wind turbine generator group including the wind turbine generators in which the temperature difference is large as the high degradation wind turbine generator group.

According to the above aspect, wind turbine generators of which the temperature difference between the detected insulator temperature information and the temperature of the insulator during a rated operation is large are treated as a high degradation wind turbine generator group, and the active power of the wind turbine generators in the high degradation wind turbine generator group is reduced prior to wind turbine generators in the other wind turbine generator groups. This can reduce Joule heating from a coil etc., reducing the time during which the insulator is exposed to high temperature, thereby reducing the risk of breaking the insulator due to a thermal stress. Here, examples of the insulator include an insulator used in a transformer and insulators in a converter and a heavy duty electrical component to which a voltage is applied.

The wind turbine generators according to the above aspect may each include a counter that counts the number of times the operating mode is switched, during a predetermined period, from a first operating mode, which is an operating mode for the case where a voltage drop on the utility grid side has not occurred, to a second operating mode, which is an operating mode for the case where a grid voltage drop of the utility grid has occurred; the estimating section may estimate the degradation levels on the basis of the numbers of times counted by the counter; and the electric power control unit may treat the wind turbine generators having the number of times more than the other wind turbine generators as the high degradation wind turbine generator group.

According to the above aspect, a wind turbine generator in which the operating mode is switched many times during a predetermined period from the first operating mode, which is an operating mode for the case where no voltage drop has occurred at the utility grid side, to the second operating mode, which is an operating mode for the case where a voltage drop of the utility grid side has occurred, is treated as a wind turbine generator with a high level of degradation. For example, in the operating mode for the case where a voltage drop of the utility grid side has occurred during a predetermined period, that is, an operating mode in which a so called LVRT (low voltage ride through) function works, the main shaft, the gearbox and so on of the wind turbine generator are subjected to a mechanical stress due to an axial torsional vibration. Since such a wind turbine generator including many mechanical parts subjected to a mechanical stress is treated as a wind turbine generator with a high level of degradation, the operation of the wind turbine generator with a high level of degradation can be reduced, thereby reducing the degradation of the whole wind power plant.

The wind turbine generators may each include a vibration measuring unit that measures the vibration of a drivetrain; the estimating section may estimate the degradation levels on the basis of the measured vibration values from the vibration measuring unit; and the electric power control unit may treat the wind turbine generator group including the wind turbine generators having the measured vibration values larger than those of the other wind turbine generators as the high degradation wind turbine generator group.

For example, rotary components, such as a bearing and a gearbox, have metal to metal sliding portions, so that if intrusion of metal powder, etc. occurs, vibrations or unusual sounds are generated during the rotation of the shaft of the drivetrain. Thus, the vibration of the drivetrain is measured by the estimating section to estimate the degradation level. For example, the degradation level is estimated on the basis of the difference between a vibration value during normal operation and a vibration value during measurement.

The estimating section according to the above aspect may calculate indices of each of the wind turbine generators for the whole wind power plant on the basis of the degradation levels; and the grouping section may have threshold values for the indices and may form the wind turbine generator groups on the basis of the threshold values and the indices.

By converting the degradation levels to indices and comparing the indices with predetermined threshold values in this way, the wind turbine generators can easily be grouped.

The grouping section according to the above aspect may form the wind turbine generator groups, upon receiving an active power reduction request from the utility grid side as a trigger.

According to the above aspect, since the wind turbine generators are grouped at the timing at which an active power reduction request is received from the utility grid side, the wind turbine generators can be grouped in accordance with the present operating state thereof, as compared with a case in which they are grouped in advance, which enables active power control according to the present degradation levels of the wind turbine generators.

In the above aspect, a timer that measures the operation times of the wind turbine generators may be provided, wherein the grouping section may form the wind turbine generator groups at predetermined time intervals measured by the timer.

Since the wind turbine generators are grouped at predetermined time intervals, active power control according to the degradation levels of the wind turbine generators, which change constantly, can be performed.

A third aspect of the present invention is a wind power plant comprising the monitoring and control apparatus and the plurality of wind turbine generators according to one of the above.

A fourth aspect of the present invention is a monitoring and control method applied to a wind power plant including a plurality of wind turbine generators, the monitoring and control method comprising: a first step of estimating the degradation levels of the wind turbine generators; a second step of grouping the wind turbine generators on the basis of the degradation levels to form the wind turbine generator groups; and a third step of controlling, upon receiving an active power reduction request from a utility grid side, reduction of the active power of the wind turbine generators included in a high degradation wind turbine generator group, which is the wind turbine generator group including the wind turbine generators with a high level of degradation, prior to the wind turbine generators included in the other wind turbine generator groups other than the high degradation wind turbine generator group.

Advantageous Effects of Invention

The present invention offers the advantage of reducing the influence on a utility grid by reducing a rapid change in active power.

The present invention also offers the advantage of extending the life of a wind power plant while controlling active power outputs in response to a request from a utility grid.

DESCRIPTION OF EMBODIMENTS

Embodiments of a monitoring and control apparatus and method and a wind power plant equipped with the same according to the present invention will be described hereinbelow with reference to the drawings.

First Embodiment

Figure 1:
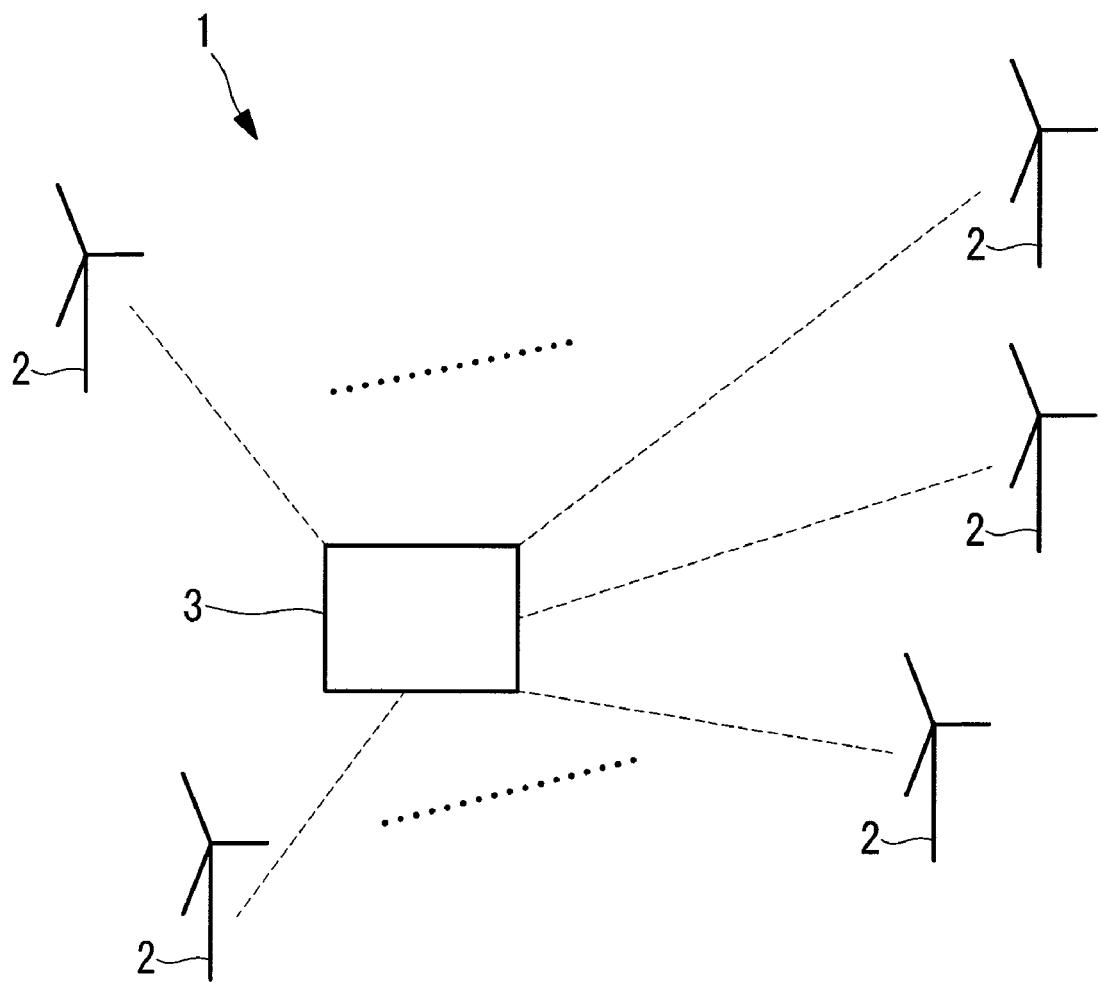
FIG. 1 is a diagram showing, in outline, the configuration of a wind power plant 1 according to a first embodiment of the present invention.

FIG. 1 is a diagram showing the overall configuration of a wind power plant 1 according to a first embodiment of the present invention. The wind power plant 1 includes a plurality of wind turbine generators (hereinafter referred to as "wind turbines") 2 and a monitoring and control apparatus 3 that controls the operating states of the individual wind turbines 2. Although this embodiment is described using an example in which the wind power plant 1 has 50 wind turbines 2, the number is not particularly limited.

Figure 2:
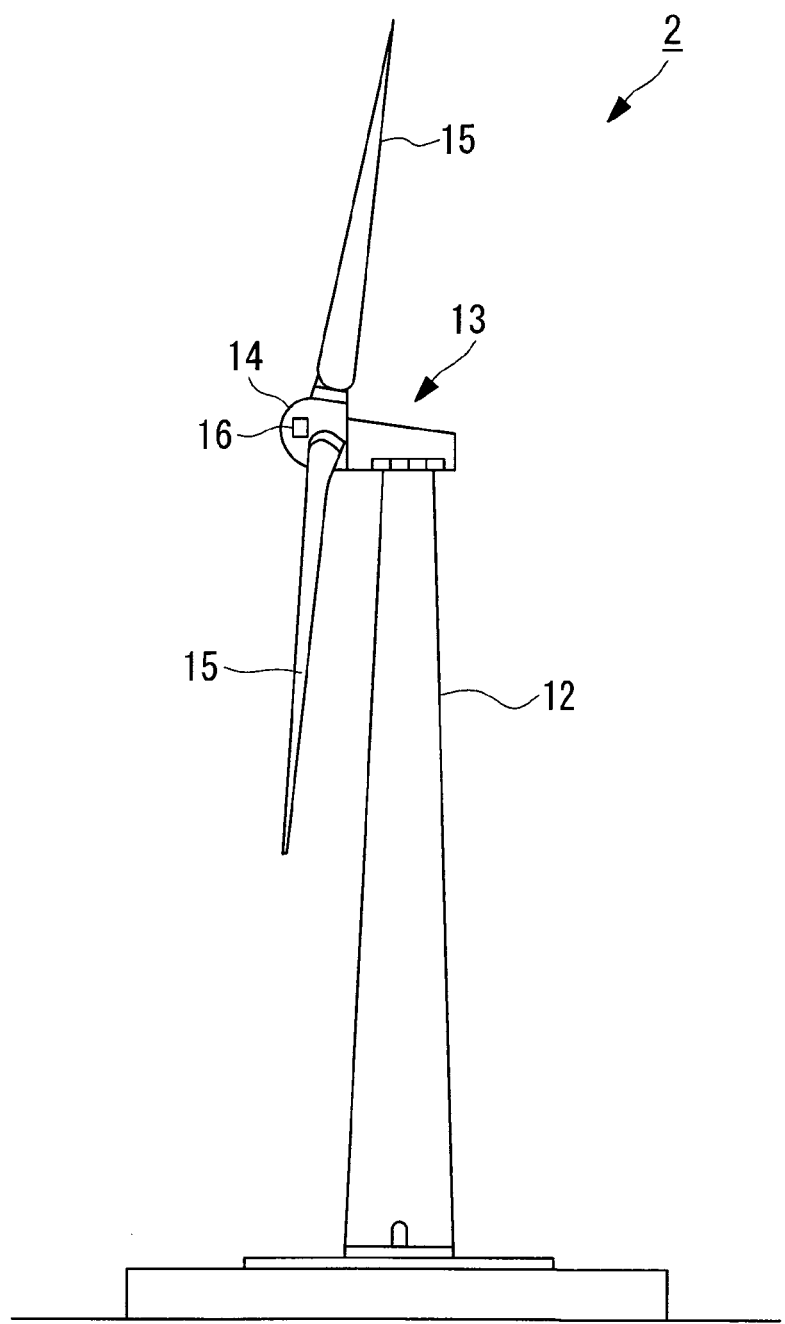
FIG. 2 is a schematic diagram showing, in outline, the configuration of a wind turbine according to the first embodiment of the present invention.

FIG. 2 is a schematic diagram showing, in outline, the configuration of the wind turbine 2. As shown in FIG. 2, the wind turbine 2 includes a tower 12, a nacelle 13 installed on the upper end of the tower 12, and a rotor head 14 provided on the nacelle 13 so as to be rotatable about the substantially horizontal axis thereof. The rotor head 14 has three wind turbine blades 15 mounted radially about its rotation axis. Thus, the force of wind blowing against the wind turbine blades 15 from the direction of the rotation axis of the rotor head 14 is converted to motive power that rotates the rotor head 14 about the rotation axis, and the motive power is converted to electrical energy by a power generating unit (not shown) provided in the wind turbine 2. The rotor head 14 also has a pitch control unit 16 that causes the wind turbine blades 15 to rotate about the axis of the wind turbine blades 15 in accordance with wind conditions to control the pitch angles etc. of the wind turbine blades 15, thereby controlling the operation of the wind turbine 2.

Although this embodiment is described as applied to a wind turbine having three wind turbine blades 15 by way of example, the number of the wind turbine blades 15 is not limited to three and may be two or more than three; it is not particularly limited.

Figure 3:
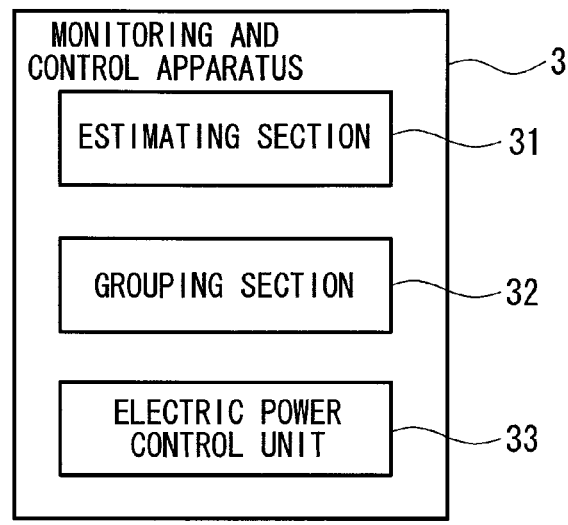
FIG. 3 is a diagram showing, in outline, the configuration of a monitoring and control apparatus according to the first embodiment of the present invention.

As shown in FIG. 3, the monitoring and control apparatus 3 includes an estimating section 31, a grouping section 32, and an electric power control unit 33. The estimating section 31 estimates the degradation level of each wind turbine 2. Here, the degradation level refers to the degree of fatigue of the wind turbine 2 determined depending on, for example, the frequency of failures of the wind turbine 2 in the past, the frequency of warnings detected from the wind turbine 2 in the past, and the poor response of the wind turbine 2. This embodiment will be described using an example in which the estimating section 31 estimates the degradation level on the basis of the power generation level of the wind turbine 2 and the temperature of an insulator of the wind turbine 2.

Figure 4:
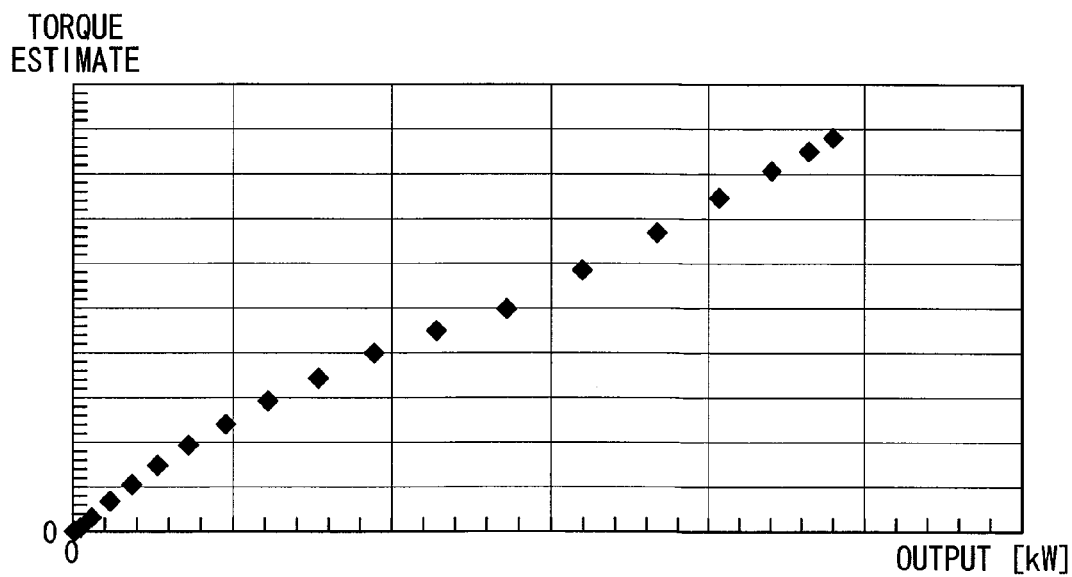
FIG. 4 is a diagram showing an example of the relationship between the output of a wind turbine generator and the torque of a drivetrain.

For example, in the case where the wind turbine 2 has a structure in which a main shaft coupled to the rotor head fitted with the wind turbine blades and rotating integrally therewith, a gearbox that increases the rotational speed of the main shaft and outputs the rotational torque, and a generator driven by the output of the gearbox are joined together to constitute a drivetrain, the relationship between the output of the wind turbine 2 and the rotational torque of the main shaft is as shown in FIG. 4. FIG. 4 shows a relationship in which the rotational torque exerted on the main shaft of the drivetrain increases as the output of the wind turbine 2 increases. Since the degradation level (fatigue) of the wind turbine 2 can be estimated from the time integrated value of the level of the rotational torque exerted on the main shaft, the estimating section 31 estimates the output of the wind turbine 2 as a degradation level (defined as a first degradation level).

The estimating section 31 also estimates a degradation level (defined as a second degradation level) on the basis of a temperature detected from an insulator of the wind turbine 2. Specifically, each wind turbine 2 is equipped with a temperature sensor (not shown) for detecting the temperature of the insulator of the wind turbine 2, and the estimating section 31 acquires the measured temperature information from each temperature sensor and uses a difference between the acquired temperature and the temperature of the insulator during rated operation as a degradation level. For example, in the case where the temperature of an insulator used in a transformer is employed as the insulator temperature information, the operation speed of a transformer cooling fan that operates in accordance with a difference in temperature may be used as the degradation level, instead of the temperature difference described above.

The plurality of degradation levels (the first degradation level and the second degradation level) estimated on the basis of a plurality of items of information, such as the power generation level of the wind turbine 2 and the temperature of the insulator of the wind turbine 2, in this way are individually output to the grouping section 32.

More preferably, in addition to the estimation of the degradation levels, the estimating section 31 calculates an index for the whole wind power plant on the basis of the estimated degradation levels and outputs the index to the grouping section 32.

For example, the estimate 31 acquires the power generation levels from the individual wind turbines 2, calculates deviation values relative to a total power generation level (kWh) of the wind power plant, and sets the values as load-fatigue evaluation indices $\alpha$. The estimating section 31 also calculates deviation values of the total number of times the transformer cooling fans are operated from the individual wind turbines 2 and sets the values as insulation-fatigue evaluation scores $\beta$.

The grouping section 32 groups the wind turbines 2 on the basis of the degradation levels to form wind turbine generator groups (hereinafter referred to as "wind turbine groups"). Furthermore, the grouping section 32 may determine the operating state of the wind turbines 2 on the basis of the active power output levels and may group wind turbines 2 while they are halted or outputting low power (for example, 500 kW) to form a wind turbine group (for example, a group D in FIG. 5) for which active power control is not performed.

Figures 5, 6:
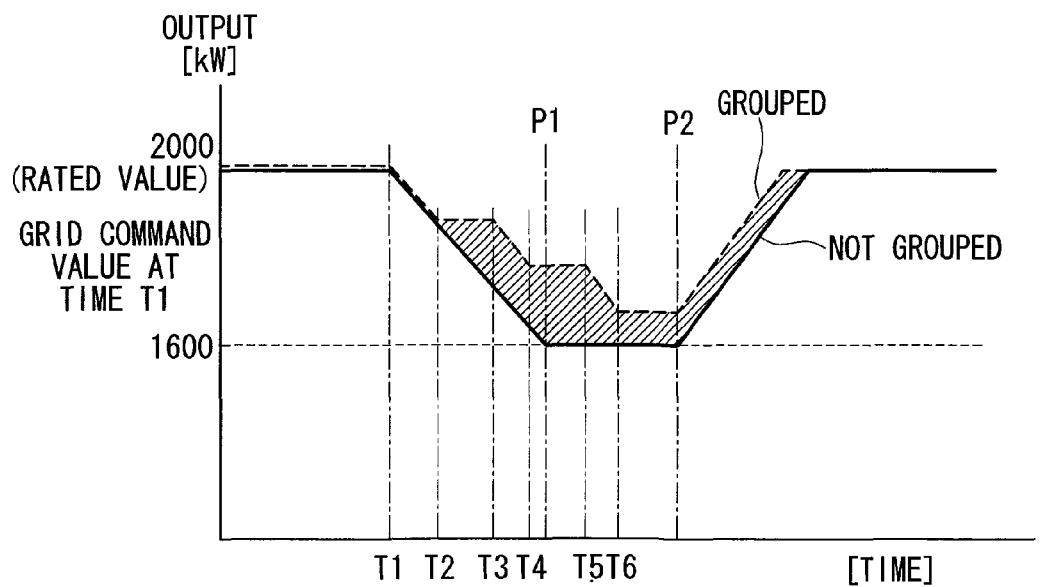
FIG. 5 is a diagram showing an example of threshold values in the case where wind turbine generator groups are formed on the basis of a load-fatigue evaluation index and an insulation-fatigue evaluation score.
FIG. 6 is a diagram showing the relationship between time and output in the case where active power is controlled for each wind turbine group.

Furthermore, if threshold values of the indices are provided, the grouping section 32 forms wind turbine groups on the basis of the threshold values and the indices. In FIG. 5, the indices (load-fatigue evaluation index $\alpha$ and the insulation-fatigue evaluation score $\beta$) and the individual threshold values for generating wind turbine groups are associated with each other. For example, as shown in FIG. 5, if the load-fatigue evaluation index $\alpha$ is written as a threshold value a<$\alpha$, the wind turbine is grouped into a wind turbine group to which significant active power limitation is imposed with priority (for example, a group A); if a threshold value b<$\alpha \leq$ the threshold value a, the wind turbine is grouped into a wind turbine group to which significant active power limitation is imposed (for example, a group B); and if $\alpha \leq$ the threshold value b, the wind turbine is grouped into a wind turbine group to which active power limitation is imposed (for example, a group C).

If there are a plurality of items of information on the degradation levels or the indices, the grouping section 32 determines a group for classification on the basis of a predetermined condition. For example, in the case where the predetermined condition is selecting a high priority group, the group for a wind turbine 2 whose load-fatigue evaluation index $\alpha$ is in the range of group C and whose insulation-fatigue evaluation score $\beta$ is in the range of group A is determined to be the high priority group A.

The grouping section 32 forms wind turbine groups at predetermined timing. For example, the grouping section 32 may form wind turbine groups upon receiving an active power reduction request from a utility grid side as a trigger, or alternatively, may be equipped with a timer that measures the operation times of the individual wind turbines 2 and may form wind turbine groups at predetermined time intervals measured by the timer.

Since the wind turbine generators are grouped at the timing of receiving an active power reduction request from the utility grid side, the wind turbines 2 can be grouped in accordance with the present operating state thereof, as compared with a case in which they are grouped in advance, which enables active power control according to the present degradation levels of the wind turbines 2. Furthermore, since the wind turbines 2 are grouped at predetermined time intervals, active power control can be performed according to the degradation levels of the wind turbines 2, which change constantly.

Upon receiving an active power reduction request from the utility grid side, the electric power control unit 33 reduces the active power of the individual wind turbines 2 in a high degradation wind turbine group including wind turbines 2 with a high level of degradation prior to wind turbines 2 included in the wind turbine groups other than the high degradation wind turbine group. Specifically, the electric power control unit 33 controls the active power of wind turbines 2 included in the plurality of wind turbine groups formed in the wind power plant at a predetermined proportion set in accordance with the degradation levels. Furthermore, the electric power control unit 33 repeats the active power control while detecting the status of the utility grid side at predetermined time intervals.

More specifically, a method for calculating active power command values that the electric power control unit 33 outputs to the individual wind turbines 2 will be described. The description is made on the assumption that the electric power control unit 33 controls the active power of group A to group C and does not control the active power of group D. Furthermore, the number of wind turbines 2 in group A is n, the number of wind turbines 2 in group B is m, and the number of wind turbines 2 in group C is l.

Assuming that a reduction in active power requested from the utility grid side to the wind power plant 1 is $\Delta P\_lim$ and that a reduction in active power requested to wind turbines 2 included in group A, which is the group to be subjected to active power control with priority, is $\Delta Pa\_lim$, $\Delta Pa\_lim$ is set at a predetermined percentage of active power output from the individual wind turbines 2 in group A (which is hereinafter described as, for example, a reduction of 20%).

The active power control is performed in accordance with the conditional expression shown in Exp. (1) below.

$$\Delta P\_lim > \Delta Pa\_lim \times n \quad (1)$$

<Case 1>

If the above Exp. (1) is satisfied, the reduction level in active power of group A remains at the preset 20%. The reduction level in active power of the individual wind turbines in group B and group C are determined using Exp. (2) below.

{Formula 1}

$$\Delta Pb\_lim = \Delta Pc\_lim = (\Delta P\_lim - \Delta Pa\_lim \times n)/(m+1) \quad (2)$$

$$\Delta Pa\_lim \geq \Delta Pb\_lim = \Delta Pc\_lim \quad (3)$$

If the above Exp. (3) is not satisfied, $\Delta Pa\_lim$ is determined again.

<Case 2>

If the above Exp. (1) is not satisfied, the reduction level in active power of the individual wind turbines in group A is determined as in Exp. (4) below.

{Formula 2}

$$\Delta Pa\_lim = \Delta P\_lim/n \quad (4)$$

In other words, for the active power of the individual wind turbines in group A, the initially set output limitation of 20% is reviewed, and a new output limitation value that further limits the output is given.

In this case, since the active power reduction request from the utility grid side is satisfied by the output limitation of group A, output limitation of group B and group C is not performed.

Thus, active power command values to be output to the individual groups are set on the basis of the number of wind turbines 2 that belong to the groups.

In addition, the electric power control unit 33 performs active power control in accordance with the degradation levels of the wind turbine groups, and therefore, in the case where there are a plurality of wind turbine groups, active power may be reduced by selecting target groups in sequence (for example, selecting group A first and group B next), or alternatively, active power may be reduced by continuously selecting the same wind turbine group a plurality of times (for example, continuously selecting group A three times) as a target group.

When switching among target groups, the electric power control unit 33 may perform the next control operation when completion of the control operation currently being performed is detected, or alternatively, timing may be done using, for example, a timer, and the next control operation may be performed after a lapse of a predetermined period after completion of the previous control operation.

Next, the operation of the wind power plant 1 according to this embodiment will be described with reference to FIGS. 1 to 6. Here, a description is given using an example in which, while the wind power plant 1 equipped with 50 wind turbines 2 having an output of 2.0 MW is operated at a rated output, a request for a 20% output reduction (for example, 20 MW) is output from the utility grid side.

When a 20%-reduction request of the power generation level (for example, 20 MW) is output from the utility grid side, the monitoring and control apparatus 3 acquires the reduction request at time T1 in FIG. 6. The grouping section 32 detects the operating states (output) of the individual wind turbines 2 in the wind power plant 1 and classifies wind turbines 2 having outputs lower than a predetermined value (for example, 500 kW) as group D, which is a wind turbine group that is not to be subjected to active power control. When the reduction request is given to the estimating section 31, individual degradation levels are estimated on the basis of the power generation levels and the temperatures of insulators of the wind turbines 2 in the wind power plant 1, and furthermore, the load-fatigue evaluation indices $\alpha$, which are indices calculated on the basis of the power generation levels, and insulation-fatigue evaluation scores $\beta$, which are indices calculated on the basis of the temperatures of the insulators of the wind turbines 2, are calculated.

In the grouping section 32, wind turbines 2 other than the wind turbines 2 classified as group D are classified as group A to group C on the basis of the threshold values specified for the load-fatigue evaluation indices $\alpha$ and the insulation-fatigue evaluation scores $\beta$ calculated for the individual wind turbines 2 (refer to FIG. 5) to form the plurality of wind turbine groups. Here, it is assumed that the wind turbine groups are determined to be wind turbine groups A, B, and C in decreasing order of priority in controlling active power; for example, the number of wind turbines 2 included in group A is 2 (that is, n=2), the number of wind turbines 2 included in group B is 18 (that is, m=18), the number of wind turbines 2 included in group C is 30 (that is, l=30), and the number of wind turbines 2 included in group D is 0.

If the number of wind turbines 2 in group A is 2, the output of group A is expressed as 2.0 MW×2=4.0 MW. The electric power control unit 33 outputs a request for a 20% output reduction as a command value to group A (high priority wind turbine group). Thus, group A is reduced in output from 4.0 MW by 4.0 MW×20%=0.8 MW in output (kW) (from time T1 to time T2 in FIG. 6). Here, for Exp. (1), since $\Delta P\_lim - \Delta Pa\_lim \times n$=20 MW−0.8 MW=19.2 MW>0, Exp. (1) is satisfied. Accordingly, Case 1 described above is selected, and output limitation of group B and group C is also performed. For the reduction request of 20 MW from the utility grid side, a further reduction of 19.2 MW is needed. In FIG. 6, there is an output reduction of 0.8 MW at time T2. On completion of the output limitation of group A, the electric power control unit 33 outputs an output reduction request to group B whose output is to be reduced next after the lapse of a predetermined period (at time T3 in FIG. 6).

Here, the number of wind turbines 2 included in group B and group C is 48. To share the remaining output reduction of 19.2 MW among the 48 wind turbines 2, a command value for reducing by 20% (=0.4 MW/2.0 MW) is determined for the wind turbines in group B and group C using Exp. (2) because 19.2 MW/48=0.4 MW. At time T3 in FIG. 6, an output reduction command value for group B is output to reduce the output of group B (from time T3 to time T4 in FIG. 6). The condition of the wind power plant 1 is checked at predetermined intervals (at time P1 in FIG. 6), and if the output reduction command from the utility grid side is continuously output, the foregoing output reduction process is continued.

Upon completion of the output reduction for group B, an output reduction command value for group C is output after the lapse of a predetermined period (at time T5 in FIG. 6) to reduce the output of group C (from time T5 to time T6 in FIG. 6). When a request for cancelling the output limitation is received from the utility grid side at time P2, the output is controlled to 100%. If there is no particular request for cancelling output limitation from the utility grid side at time P2, the output limited state is continued.

In addition, specifically, the electric power control unit 33 reduces the output of the individual wind turbines 2 by controlling the pitch angle of the wind turbine blades 15 (for example, controlling the blades 15 to the feather side), field control, or the like.

Thus, in the case where output limitation is required by a predetermined time (for example, time T6=5 minutes later) without the responsiveness requirement, stepwise output control is performed by limiting the active power for the individual wind turbines 2 included in the wind turbine group (group). This can reduce a power generation loss (for example, a loss corresponding to the hatched portion in FIG. 6) as compared with a case where the active power of all the wind turbines 2 included in the wind power plant 1 is rapidly limited.

As has been described above, with the monitoring and control apparatus and method according to this embodiment, as well as the wind power plant equipped with the same, when an active power reduction request is received from the utility grid side, wind turbines 2 in a high degradation wind turbine group among the wind turbine groups grouped according to the degradation levels of the wind turbines 2 are reduced in active power prior to wind turbines 2 in the other wind turbine groups. Since the active power of a wind turbine group with a high level of degradation is reduced with priority in this way, a rapid change in active power caused when the active power of all the wind turbines 2 in the wind power plant is limited can be reduced, and thus the influence on the utility grid can be reduced.

Furthermore, since the active power of a wind turbine group with a high level of degradation (that is, wind turbine generators with a high level of degradation due to operation) is reduced with priority, reduction of the active power of wind turbine groups with a low level of degradation (that is, wind turbine generators with a low level of degradation due to operation) is delayed, which results in an increase in the life of the wind power plant. Furthermore, reducing the active power in units of wind turbine groups decreases variations in active power per wind turbine 2, as compared with a case in which single wind turbines 2 respond to active power reduction requests.

Modification 1

While the embodiment has been described as applied to a case in which the estimating section 31 estimates the degradation levels on the basis of the power generation levels of the wind turbines 2 and the temperatures of the insulators, the present invention is not limited thereto. For example, if the wind turbines 2 each have a load reducing unit for reducing a load imposed on the wind turbines 2, the estimating section 31 may estimate the number of failures of the load reducing unit as a degradation level. In this case, the electric power control unit 33 treats a wind turbine group including wind turbines 2 that fail more than the other wind turbines 2 as a high degradation wind turbine group and controls the active power thereof.

This can reduce the active power of ineffective wind turbines 2 whose load cannot be reduced because of the influence of the failure of the load reducing unit prior to the other wind turbines 2, thus extending the life of the wind power plant. Here, examples of the load reducing unit include an individual pitch control unit, which is a unit for controlling the pitch angles of the wind turbine blades so as to reduce the load imposed on the wind turbine blades, and a tower damping control unit, which is a unit for controlling the damping of the wind turbine tower due to pitch angle control on the wind turbine blades.

Modification 2

Furthermore, for example, if the wind turbines 2 have a counter for counting the number of times the operating mode is switched, during a predetermined period, from a first operating mode, which is an operating mode for the case where no voltage drop has occurred at the utility grid side, to a second operating mode, which is an operating mode for the case where a grid voltage drop of the utility grid has occurred, the estimating section 31 may use the number of times counted by the counter as a degradation level. In this case, the electric power control unit 33 treats wind turbines 2 that are switched more than the other wind turbines 2 as wind turbine generators in a high degradation wind turbine group and performs active power reduction control thereon. For example, if an operating mode for the case where a voltage drop of the utility grid side has occurred during a predetermined period is set at an operating mode in which a so called LVRT function works, a wind turbine group including wind turbines 2 that are often switched from the first operating mode to the LVRT function is treated as a high degradation wind turbine group.

In the case of operation using the LVRT function, the main shafts, the gearboxes and so on of the wind turbines 2 are subjected to a mechanical stress due to an axial torsional vibration. Since such wind turbines 2 including many mechanical parts subjected to a mechanical stress are treated as wind turbines 2 in a high degradation wind turbine group, the life of the whole wind power plant can be extended.

Modification 3

Furthermore, for example, if the wind turbines 2 have a vibration measuring unit that measures the vibration of the drivetrain, the estimating section 31 may estimate the degradation level on the basis of the measured vibration value of the vibration measuring unit. In this case, the electric power control unit 33 treats a wind turbine generator group including wind turbines 2 having a measured vibration value higher than those of the other wind turbines 2 as a high degradation wind turbine generator group.

For example, rotary components, such as a bearing and a gearbox, have metal to metal sliding portions, so that if, for example, intrusion of metal powder, etc. occurs, vibrations or unusual sounds are generated during the rotation of the shaft of the drivetrain. Thus, the vibration of the drivetrain is measured by the estimating section 31 to estimate the degradation level. Specifically, the degradation level is estimated on the basis of the difference between a vibration value during normal operation and a vibration value during measurement.

In the above described embodiments, the wind turbines are grouped on the basis of the degradation levels and the active power of the wind turbines with a high level of degradation is reduced with priority. In this way, stepwise output limitation of the active power of the wind turbines in the wind power plant is performed. Thus, the influence on the utility grid is reduced by reducing the rapid change in the active power. The present invention, however, is not limited to the above described embodiments. For example, when an active power reduction request from the utility grid side is output, the present invention may reduce the rapid change in the active power by reducing the output of all wind turbines in the wind power plant in a stepwise manner.

In addition, the wind turbines may be grouped, not on the basis of the degradation levels, but arbitrarily. The output limit to the wind turbines is performed per group in order. In this way, the present invention may reduce the rapid change in the active power by reducing the total power generation level of the wind power plant in a stepwise manner.

REFERENCE SIGNS LIST 1 wind power plant
2 wind turbine generator
3 monitoring and control apparatus
31 estimating section
32 grouping section
33 electric power control unit

The invention claimed is:

1. A monitoring and control apparatus for a wind power plant including a plurality of turbine generators, comprising:
   a grouping section that groups the wind turbine generators in the wind power plant to form a plurality of groups;
   an electric power control unit for controlling the wind turbine generators and reducing the output of the wind power plant in a stepwise manner by instructing an output limit to the wind turbine generators; and,
   wherein the electric power control unit selects in sequence target groups of wind turbine generators to which the output limit is instructed when an active power reduction request from a utility grid side is outputted.

2. The monitoring and control apparatus according to claim 1, wherein
   the grouping section groups each of the wind turbine generators on the basis of a degradation level of each of the wind turbine generators.

3. The monitoring and control apparatus according to claim 2, wherein
   the degradation level is calculated on the basis of at least one of load fatigue and insulation fatigue of each of the wind turbine generators.

4. A monitoring and control apparatus applied to a wind power plant including a plurality of wind turbine generators, comprising:
   an estimating section that estimates degradation levels of each of the wind turbine generators;
   a grouping section that groups the wind turbine generators on the basis of the degradation levels to form wind turbine generator groups; and
   an electric power control unit that reduces, upon receiving an active power reduction request from a utility grid side, the active power of the wind turbine generators included in a high degradation wind turbine generator group, which is the wind turbine generator group including the wind turbine generators with a high level of degradation, prior to the wind turbine generators included in the other wind turbine generator groups other than the high degradation wind turbine generator group.

5. The monitoring and control apparatus according to claim 4, wherein
   the estimating section estimates the degradation levels on the basis of the power generation levels of the active power of the wind turbine generators; and
   the electric power control unit treats the wind turbine generator group including the wind turbine generators that produce higher power generation levels than the other wind turbine generators as the high degradation wind turbine generator group.

6. The monitoring and control apparatus according to claim 4, wherein
   in the case where the wind turbine generators each include a load reducing unit that reduces a load imposed on the wind turbine generators,
   the estimating section estimates the degradation levels on the basis of the numbers of failures of the load reducing units; and
   the electric power control unit treats the wind turbine generator group including the wind turbine generators that fail more than the other wind turbine generators as the high degradation wind turbine generator group.

7. The monitoring and control apparatus according to claim 4, wherein
   the estimating section estimates the degradation levels on the basis of the difference between a temperature detected from an insulator of the wind turbine generators and the temperature of the insulator detected during rated operation; and
   the electric power control unit treats the wind turbine generator group including the wind turbine generators in which the temperature difference is large as the high degradation wind turbine generator group.

8. The monitoring and control apparatus according to claim 4, wherein
   the wind turbine generators each include a counter that counts the number of times the operating mode is switched, during a predetermined period, from a first operating mode, which is an operating mode for the case where a voltage drop on the utility grid side has not occurred, to a second operating mode, which is an operating mode for the case where a grid voltage drop of the utility grid has occurred;
   the estimating section estimates the degradation levels on the basis of the numbers of times counted by the counter; and
   the electric power control unit treats the wind turbine generator group including the wind turbine generators having the number of times more than the other wind turbine generators as the high degradation wind turbine generator group.

9. The monitoring and control apparatus according to claim 4, wherein
   the wind turbine generators each include a vibration measuring unit that measures the vibration of a drivetrain;
   the estimating section estimates the degradation levels on the basis of the measured vibration values from the vibration measuring unit; and
   the electric power control unit treats the wind turbine generator group including the wind turbine generators having the measured vibration values larger than those of the other wind turbine generators as the high degradation wind turbine generator group.

10. The monitoring and control apparatus according to claim 4, wherein
the estimating section calculates indices of each of the wind turbine generators for the whole wind power plant on the basis of the degradation levels; and
the grouping section has threshold values for the indices and forms the wind turbine generator groups on the basis of the threshold values and the indices.

11. The monitoring and control apparatus according to claim 4, wherein the grouping section forms the wind turbine generator groups, upon receiving an active power reduction request from the utility grid side as a trigger.

12. The monitoring and control apparatus according to claim 4, comprising
a timer that measures the operation times of the wind turbine generators, wherein
the grouping section forms the wind turbine generator groups at predetermined time intervals measured by the timer.

13. A wind power plant, comprising:
a plurality of wind turbine generators;
a monitoring and control apparatus;
an estimating section that estimates degradation levels of each of the wind turbine generators;
a grouping section that groups the wind turbine generators on the basis of the degradation levels to form wind turbine generator groups; and
an electric power control unit that reduces, upon receiving an active power reduction request from a utility grid side, the active power of the wind turbine generators included in a high degradation wind turbine generator group, which is the wind turbine generator group including the wind turbine generators with a high level of degradation, prior to the wind turbine generators included in the other wind turbine generator groups other than the high degradation wind turbine generator group.

14. A monitoring and control method applied to a wind power plant including a plurality of wind turbine generators, the monitoring and control method comprising:
a first step of estimating the degradation levels of the wind turbine generators;
a second step of grouping the wind turbine generators on the basis of the degradation levels to form the wind turbine generator groups; and
a third step of controlling, upon receiving an active power reduction request from a utility grid side, reduction of the active power of the wind turbine generators included in a high degradation wind turbine generator group, which is the wind turbine generator group including the wind turbine generators with a high level of degradation, prior to the wind turbine generators included in the other wind turbine generator groups other than the high degradation wind turbine generator group.

* * * * *